United States Patent [19]
Müller et al.

[11] Patent Number: 5,241,081
[45] Date of Patent: Aug. 31, 1993

[54] N-ALKYL-N-(METH)ACRYLOYLOXYALK-YLCARBOXAMIDES OF AROMATIC CARBOXYLIC ACIDS AND AROMATIC CARBOXYLIC ACID ANHYDRIDES, AND ADHESIVES CONTAINING THESE COMPOUNDS

[75] Inventors: Michael Müller, Bergisch Gladbach; Wolfgang Podszun, Cologne; Werner Finger, Dormagen; Jens Winkel, Cologne, all of Fed. Rep. of Germany

[73] Assignee: Bayer Aktiengesellschaft, Leverkusen, Fed. Rep. of Germany

[21] Appl. No.: 743,535

[22] Filed: Aug. 9, 1991

[30] Foreign Application Priority Data

Aug. 15, 1990 [DE] Fed. Rep. of Germany ....... 4025784
Dec. 11, 1990 [DE] Fed. Rep. of Germany ....... 4039440

[51] Int. Cl.$^5$ ............... C08F 222/16; C07D 493/00; C07D 69/34
[52] U.S. Cl. .................... 549/232; 526/215; 526/269; 526/271; 526/272; 526/306; 526/318; 526/936; 106/35; 549/236; 549/244; 549/557; 560/129; 560/180; 560/183; 560/196; 560/199; 562/442; 562/443; 562/444; 562/450; 562/460; 562/489
[58] Field of Search ............... 549/232, 236, 244, 557; 562/442, 443, 460, 444; 560/196, 129, 180, 183, 199; 106/35; 564/164; 526/215, 269, 272, 306

[56] References Cited

U.S. PATENT DOCUMENTS 4,148,988  7/1979  Masuhara et al. ............... 526/318

FOREIGN PATENT DOCUMENTS 0266220  5/1988  European Pat. Off. .
0377072  7/1990  European Pat. Off. .
3510962  10/1985  Fed. Rep. of Germany .

OTHER PUBLICATIONS

Computer printout of CAS–online.
Kataoka et al, CA 105-200516w (1986).
Proc. Natl. Sci. Counc. ROC(B), vol. 8, No. 2, 1984, pp. 187–192.
Dental Materials Journal 7(2): 141–150, 1988.
Journal of Biomedical Materials Research, vol. 18, 1089–1103 (1984).
Dirass Report, E 9–4, Jul., 1987, Dia Research Institute, Inc. "Biocompatible Materials for the Oral Cavity".
Adhesive Bonding to Dentin, vol. 61, No. 9, pp. 1070–1076.

*Primary Examiner*—Cecilia Tsang
*Attorney, Agent, or Firm*—Sprung Horn Kramer & Woods

[57] ABSTRACT

The invention relates to new N-alkyl-N-(meth)acryloyloxyalkylcarboxamides of aromatic carboxylic acids and aromatic carboxylic acid anhydrides, their preparation and formulations of these compounds for use as adhesives for the treatment of dental hard substance.

8 Claims, No Drawings

N-ALKYL-N-(METH)ACRYLOYLOXYALKYLCARBOXAMIDES OF AROMATIC CARBOXYLIC ACIDS AND AROMATIC CARBOXYLIC ACID ANHYDRIDES, AND ADHESIVES CONTAINING THESE COMPOUNDS

The invention relates to new N-alkyl-N-(meth)acryloyloxyalkylcarboxamides of aromatic carboxylic acids and aromatic carboxylic acid anhydrides, their preparation and formulations of these compounds for use as adhesives for the treatment of dental hard substance.

A particularly serious problem of conservative dentistry is permanent glueing, without gaps at the edge, of filling materials made of plastic to the dental hard substance (dentine and dental enamel). Polymeric materials which harden are used as filling materials for dental repairs in the dental sector. Acrylate-based fillings, which shrink during hardening and thus contribute to the formation of gaps at the edges, are preferred as the polymeric materials which harden.

These polymeric fillings furthermore have the disadvantage that they remain poorly stuck to the dentine. To solve this problem, undercuts in the dentine have sometimes been made; for this it has been necessary to remove considerable amounts of fresh dentine, beyond the region affected. According to another method, the dentine and the enamel surface are etched superficially with acids, such as, for example, phosphoric acid, and the filling is then undertaken. Apart from the fact that the acid has an irritating effect in the oral region, it also easily penetrates through the dental canaliculi into the tooth and damages the nerve (pulp). Substance mixtures of 4-methacryloyloxyethyl trimellitate (4-MET) or the 4-methacryloyloxyethyl ester of trimellitic anhydride (4-META) with ethylenically unsaturated monomers and free radical initiators are described as adhesion promoters for fillings in the dental sector in U.S. Pat. No. 4,148,988. A commercial product based on 4-META (Superbond from Sun Medical) has to be mixed with methyl methacrylate (MMA), polymethyl methacrylate (PMMA) and partly oxidised tri-n-butylborane (TBB) to obtain the form ready for application (MMA-4-META-TBB resin/Y.-S. Kuo, Proc. Natl. Sci., Counc ROC (B) Volume 8, No. 2 (1984), 187-192). Mixtures of 4-META. of similarly complicated build-up and with the addition of a polyfunctional (meth)acrylate are also described (EP 266 220). Corresponding mixtures containing isomeric methacryloyloxyethyl esters of naphthalenetricarboxylic anhydride (4-MENTA) are also known (I. Harashima et al., Dental Materials Journal 7, 2 (1988) 141-150). Although DOS (German Published Specification) 3,510,962 states that a chloroform solution of 4-MENTA can also be used without further additives, an additional operating step is then necessary for subsequent application of MMA, PMMA and TBB. None of these adhesion promoters is capable of producing fillings free from gaps at the edges; an optimised photochemically initiated adhesive based on 4-META also gave gaps at the edges both in the enamel and in the dentine region of a filling made of plastic (K. Nagata et al., Journal of Biomedical Materials Research 18 (1984) 1089-1103). The fact that the enamel and dentine regions of one and the same cavity must be treated with different etching or cleaning solutions has been pointed out elsewhere as a further hindrance to the use of the 4-META-containing Superbond (Dirass Report E 9 - 4, Biocompatible Materials for the Oral Cavity, Dia Research Institute Inc., 1987).

A monomer related to 4-META. for use in dental adhesion promoters was reported with pyromellitic acid di-2-methacryloyloxyethyl ester (PMDM) (R. L. Bowen et al., J. Dent. Res. 61, 9 (1982) 1070-1076), this also being employed in a commercial product (Tenure from Den Mat). The use of this product is also described as complicated in the above literature reference, since the dentine must be treated with a surface-active comonomer in an additional operating step before application of the adhesion promoter. This product has also been incapable of ensuring fillings free from gaps at the edges.

It has now been found that adhesives for the treatment of dental hard substance which allow glueings which are free from gaps at the edges, coupled with a simple composition and easy handling, can be formulated with the aid of the new N-alkyl-N-(meth)acryloyloxyalkylcarboxamides of aromatic carboxylic acids and aromatic carboxylic acid anhydrides (I).

The new compounds correspond to the formula (I)

in which
X represents an N-alkyl-N-(meth)acryloyloxyalkylcarboxamide of the formula

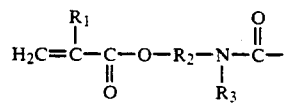

wherein
R₁ denotes hydrogen or methyl,
R₂ denotes a divalent aliphatic radical ($C_2$-$C_6$) and
R₃ denotes a monovalent aliphatic radical ($C_1$-$C_4$),
Y represents COOH, it also being possible for adjacent groups Y to be linked to form an anhydride group

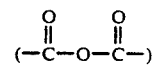

Z represents H, X or, if Y denotes COOH, Y and
Ph represents a tri- or tetrasubstituted benzene ring (1,2,3-/1,2,4- or 1,2,4,5-substitution) or a tri- or tetrasubstituted naphthalene ring (1,2,6-/1,4,5-/2,3,6-/1,4,5,8- or 2,3,6,7-substitution).

(Meth)acryloyl derivatives in the context of the present compound ar derivatives of acrylic acid and of methacrylic acid.

The various substituents and alkyl and aryl radicals of the N-alkyl-N-(meth)acryloyloxyalkylcarboxamides according to the invention in the context of the general formula (I) in general have the following meaning:

A divalent aliphatic $C_2$-$C_6$- radical ($R_2$) in general denotes a divalent straight-chain or branched hydrocarbon radical having 2 to 6, preferably 2 or 3, carbon atoms. The following divalent aliphatic radicals may be mentioned as examples: butanediyl, dimethylethanediyl, pentanediyl, neopentanediyl, hexanediyl, 2,3-dimethylbutanediyl, methylethanediyl, propanediyl and ethanediyl. Ethanediyl and propanediyl are the preferred divalent radicals.

A monovalent aliphatic $C_1$-$C_4$- radical ($R_3$) in general denotes a straight-chain or branched hydrocarbon radical having 1 to 4, preferably 3 or 4, carbon atoms. The following alkyl radicals may be mentioned as examples: methyl, ethyl, propyl, isopropyl, butyl, isobutyl and tert.-butyl. tert.-Butyl and isobutyl are particularly preferred.

Z in the context of the general formula (I) denotes hydrogen (H) or an N-alkyl-N-(meth)acryloyloxyalkyl-carboxamide of the formula

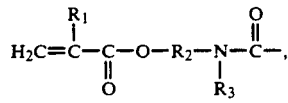

wherein $R_1$, $R_2$ and $R_3$ have the meanings given, or also COOH, if Y also denotes COOH.

Y can also represent, in addition to COOH, an anhydride group if the two radicals containing Y are bonded to adjacent positions on an aromatic. Adjacent here means ortho-positions in the benzene or naphthalene nuclei and the α-positions (1,8- or 4,5-substitution) in the naphthalene nuclei.

Ph denotes a benzene nucleus which is trisubstituted by X and Y in the 1,2,3- or 1,2,4-position or tetrasubstituted by X, Y and Z in the 1,2,4,5-position, or a naphthalene nucleus which is trisubstituted by X and Y in the 1,2,6-, 1,4,5- or 2,3,6-position or tetrasubstituted by X, Y and Z in the 2,3,6,7- or 1,4,5,8-position.

Preferred compounds in the context of the formula (I) correspond to the formula (II)

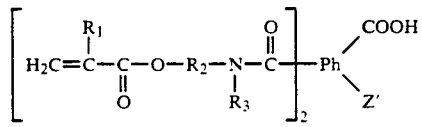

in which $R_1$ denotes hydrogen or methyl, $R_2$ denotes a divalent aliphatic radical ($C_2$-$C_6$), $R_3$ denotes a monovalent aliphatic radical ($C_1$-$C_4$), Z' denotes hydrogen or COOH and Ph represents a tri- or tetrasubstituted benzene ring (1,2,3-/1,2,4- or 1,2,4,5-substitution) or a tri- or tetrasubstituted naphthalene ring (1,2,6-/1,4,5-/2,3,6-/1,4,5,8- or 2,3,6,7-substitution).

Another preferred group of compounds of the formula (I) corresponds to the formula (III)

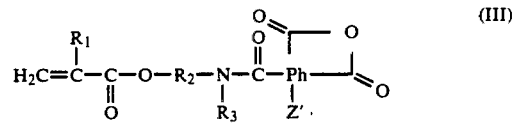

in which $R_1$ denotes hydrogen or methyl, $R_2$ denotes a divalent aliphatic radical ($C_2$-$C_6$), $R_3$ denotes a monovalent aliphatic radical ($C_1$-$C_4$), Z' denotes hydrogen or COOH and Ph represents a benzene ring which is tri- or tetrasubstituted (1,2,3-/1,2,4- or 1,2,4,5-substitution) or a tri- or tetrasubstituted naphthalene ring (1,2,6-/1,4,5-/2,3,6-/1,4,5,8- or 2,3,6,7-substitution).

A particularly preferred group of compounds of the formula (I) corresponds to the formula (IV)

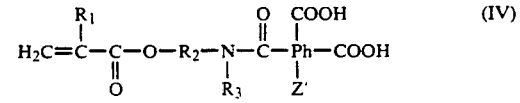

in which $R_1$ denotes hydrogen or methyl, $R_2$ denotes a divalent aliphatic radical ($C_2$-$C_6$), $R_3$ denotes a monovalent aliphatic radical ($C_1$-$C_4$), Z' denotes hydrogen or COOH and Ph represents a tri- or tetrasubstituted benzene ring (1,2,3-/1,2,4- or 1,2,4,5-substitution) or a tri- or tetrasubstituted naphthalene ring (1,2,6-/1,4,5-/2,3,6-/1,4,5,8- or 2,3,6,7-substitution).

The following N-alkyl-N-(meth)acryloyloxyalkyl-carboxamides may be mentioned specifically as examples:

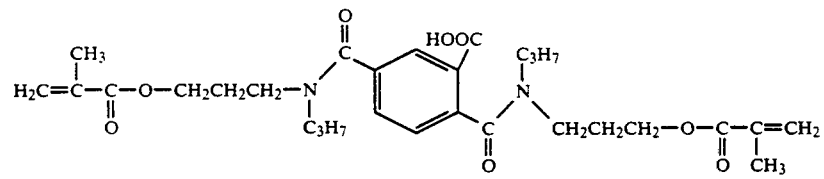

(X)

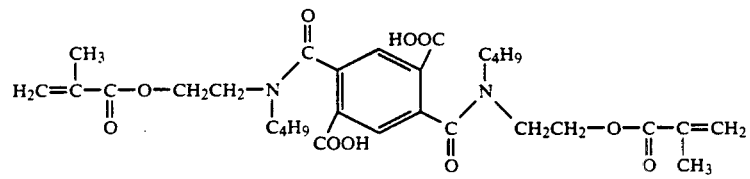

(XI)

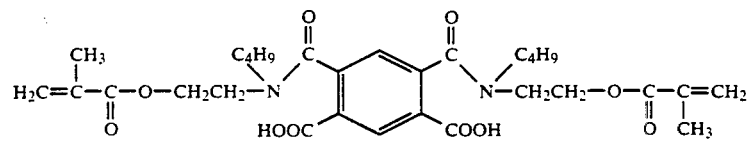

-continued
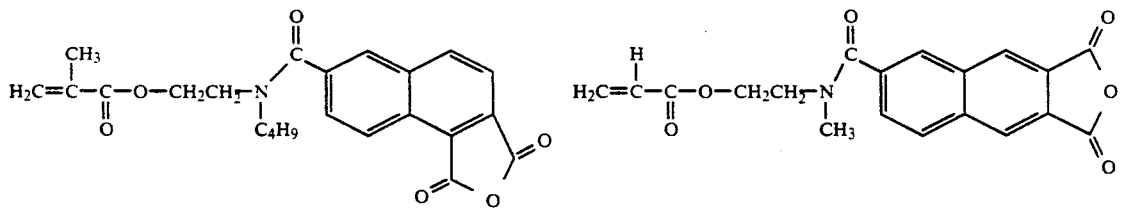
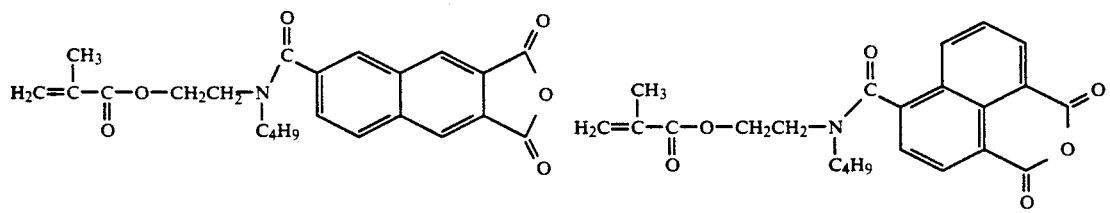
(VIII)
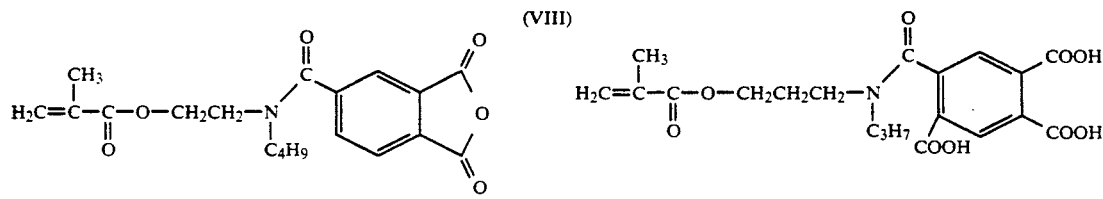
(XIII) (XIV)
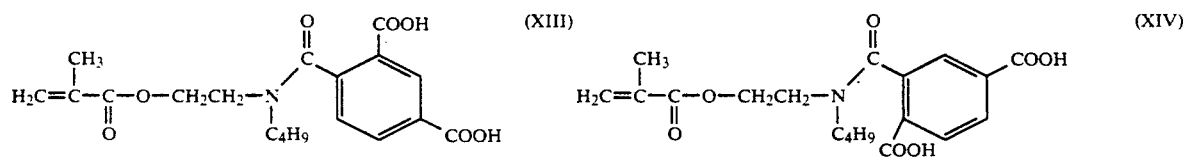
(XII) (IX)
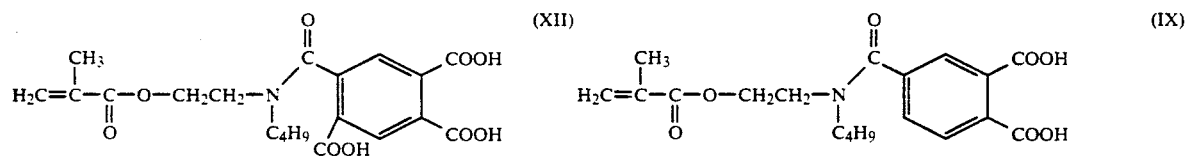
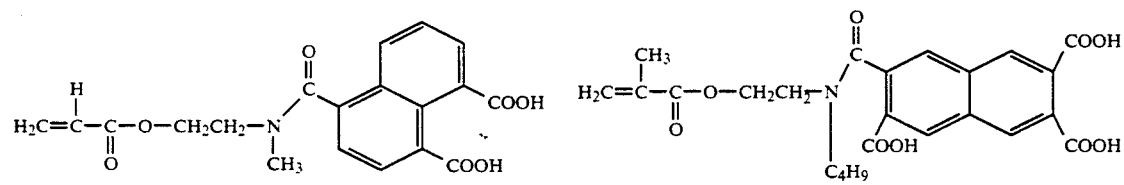
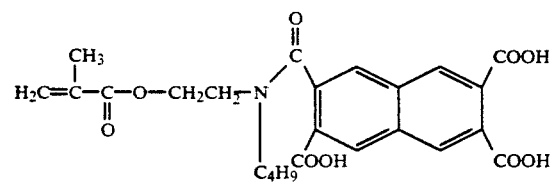
A process has furthermore been found for the preparation of N-alkyl-N(meth)acryloyloxyalkylcarboxamides of aromatic carboxylic acids and aromatic carboxylic acid anhydrides of the formula (i), which is characterised in that monoanhydrides of the formula (V)
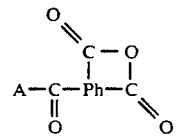
(V)
or dianhydrides of the formula (VI)

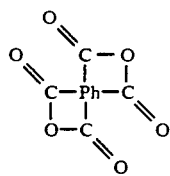

wherein

A denotes hydroxyl (OH) or chlorine (Cl) and

Ph represents a tri- or tetrasubstituted benzene ring (1,2,3-/1,2,4- or 1,2,4,5-substitution) or a tri- or tetrasubstituted naphthalene ring (1,2,6-/1,4,5-/2,3,6-/1,4,5,8- or 2,3,6,7-substitution) are reacted with an amine of the formula (VII)

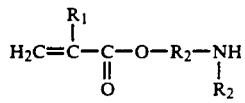

in which $R_1$ denotes hydrogen or methyl, $R_2$ denotes a divalent aliphatic radical ($C_2$–$C_6$) and $R_3$ denotes a monovalent aliphatic radical ($C_1$–$C_4$), in an organic solvent at between $-30°$ and $110°$ C., if appropriate in the presence of a base, and if appropriate the resulting product is hydrolysed with water at between $5°$ and $100°$ C.

Monoanhydrides of the formula (V) which are preferably employed in the process according to the invention are the commercially available trimellitic acid derivatives 1,2,4-benzenetricarboxylic acid anhydride chloride and 1,2,4-benzenetricarboxylic acid anhydride, the hemimellitic acid derivatives, known from the literature, 1,2,3-benzenetricarboxylic acid anhydride (Beilstein Volume H/18, page 468, 4th edition, Springer Verlag 1934) and 1,2,3-benzenetricarboxylic acid anhydride chloride (U.S. Pat. No. 3,920,667), and the naphthalenetricarboxylic acid derivatives 1,2,6-, 2,3,6- and 1,4,5-naphthalenetricarboxylic acid anhydride chloride prepared by Harashima et al. (Dental Materials Journal 7 (1988) 142).

Preferred dianhydrides of the formula (VI) which may be mentioned are the commercially available compounds benzene-1,2,4,5-tetracarboxylic acid dianhydride (pyromellitic dianhydride) and naphthalene-1,4,5,8-tetracarboxylic acid dianhydride, and naphthalene-2,3,6,7-tetracarboxylic acid dianhydride, which is easily formed by dehydration from the known naphthalene-2,3,6,7-tetracarboxylic acid (Chiba et al., Chem. Lett. 11 (1988) 1933–1936).

Aminoalkyl (meth)acrylates of the formula (VII) are commercially available or can be prepared in a known manner by esterification of alkanolamines, if appropriate using protective groups for the amino function.

Suitable organic solvents for the process according to the invention are aprotic solvents, such as dioxane, tetrahydrofuran,N,N-dimethylformamide,N,N-dimethylacetamide, dimethyl sulphonamide and acetone. Toluene and diethyl ether are preferably suitable. Xylene, methylene chloride, chloroform and methyl tert.-butyl ether are particularly preferred.

A suitable temperature range for the reaction of the amine VII is between $-30°$ and $110°$ C. This reaction is preferably carried out at between $-10°$ and $50°$ C., and particularly preferably at between $-5°$ and $30°$ C. Inorganic or organic bases can additionally be used in the process according to the invention.

Preferred inorganic bases are the weakly basic carbonates and bicarbonates of sodium and potassium. Preferred organic bases are tertiary amines, triethylamine and pyridine being particularly preferred. The bases are employed in an equimolar to five times the molar amount in respect of the anhydride of the formula (V) or (VI) employed, a 2- to 3-fold molar excess being preferred. The organic bases in this manner additionally act as solubilising agents. Nevertheless, it may also be advantageous to carry out the process according to the invention in a supersaturated solution of the anhydride (V) or (VI), that is to say in a dispersion, since the reaction product is more readily soluble than the anhydride and the anhydride is consequently dissolved as the reaction progresses. To prepare the derivatives with adjacent carboxylic acid groups of the general formula (I), the anhydrides obtained in the above process are hydrolysed at temperatures between $5°$ and $100°$ C., and preferably between $20°$ and $50°$ C. This can be effected either after isolation of the anhydrides of the general formula (I) or without isolation, by direct hydrolysis of the reaction mixture. To carry out this hydrolysis, an equimolar amount, but preferably more than ten times the molar amount, of water is added. It is a particular feature of the process according to the invention that it may be advantageous that the water added does not have to be miscible with the solvent used in the reaction. Precisely hydrolysis in a two-phase mixture is preferred, since in this case the most reactive anhydride group and not the amide and ester bonds in the compound (I) according to the invention is attacked in a targeted manner.

In a particular embodiment of the process according to the invention, the water can also be added in an amount less than the equimolar amount, or the addition of water can also be dispensed with completely. This is the case if carbonates or bicarbonates have been used beforehand in the reaction between the anhydrides (V) or (VI) and the amine (VII). The carbonates and bicarbonates liberate water of reaction in the course of this reaction, and this causes the intended hydrolysis of the anhydride group.

The hydrolysis described here can moreover be catalysed by controlled addition of acids, above all sulphuric acid, phosphoric acid or toluenesulphonic acid, or acid ion exchangers, or by addition of bases, such as sodium hydroxide, carbonate or bicarbonate and potassium hydroxide, carbonate or bicarbonate.

A general synthesis will be described below to illustrate the process according to the invention. The amine (VII) is added dropwise to a solution of the anhydride (V) and an excess of base in an organic solvent at room temperature and the mixture is then stirred at elevated temperature until, according to monitoring by IR, the amine (VII) has been consumed. Water is then added in excess and the corresponding mixture is thoroughly stirred vigorously at elevated temperature until anhydride bands are no longer visible in the IR spectrum of the mixture. The product according to the invention formed can be extracted as the anion in an alkaline aqueous phase and isolated from this after acidification.

The aromatic carboxylic acid obtained after the hydrolysis can also be converted back, if it contains adjacent carboxylic acid groups, into the corresponding anhydride by heating with acetic anhydride in an organic aprotic solvent. The anhydrides are obtained in this manner in a particularly high purity.

The formulations according to the invention of the new N-alkyl-N-(meth)acryloyloxyalkylcarboxamides (I) comprise, in addition to these carboxamides, a solvent and if appropriate initiators, coactivators and (meth)acrylic acid esters which can form crosslinkings. In particular, mixtures of various carboxamides (I) according to the invention can also be employed in the formulations according to the invention.

The solvents in the context of the formulations according to the invention should dissolve the components and should, because of the use, be non-toxic. Preferred solvents which may be mentioned are water and volatile organic solvents, such as methanol, ethanol, propanol, isopropanol, acetone, methyl ethyl ketone, methyl or ethyl acetate and tetrahydrofuran. In general, 10 to 1000 parts by weight, preferably 50 to 300 parts by weight, of the solvent, based on the carboxamide (I), are employed. Mixtures of these solvents may also be particularly preferred, aqueous mixtures being especially preferred.

Initiators in the context of the present invention are agents which form free radicals and which induce free radical polymerisation. Photoinitiators which induce free radical polymerisation under the action of light, for example UV light, visible light or laser light, are preferred.

The so-called photopolymerisation initiators are known per se (Houben Weyl, Methoden der organischen Chemie (Methods of Organic Chemistry), Volume E 20, page 80 et seq., Georg Thieme Verlag Stuttgart, 1987). They are preferably mono- or dicarbonyl compounds, such as benzoin and derivatives thereof, in particular benzoin methyl ether, benzil and benzil derivatives, for example 4,4-oxydibenzil, and other dicarbonyl compounds, such as diacetyl, 2,3-pentanedione and α-diketo derivatives of norbornane and substituted norbornanes, metal carbonyls, such as pentacarbonylmanganese, or quinones, such as 9,10-phenanthrenequinone and naphthoquinone. Camphorquinone is particularly preferred.

The formulations according to the invention in general contain 0.01 to 2 parts by weight, preferably 0.1 to 0.5 part by weight, of the initiator per part by weight of the carboxamide (I).

If one of the components to be joined which is in contact with the adhesive component according to the invention already contains an initiator of the type described, the initiator in the adhesive component can also be dispensed with completely.

It may be advantageous to add coactivators which accelerate the polymerisation reaction to the formulations according to the invention. Examples of known accelerators are amines, such as p-toluidine, dimethyl-p-toluidine, trialkylamines, such as trihexylamine, polyamines, such as N,N,N',N'-tetraalkylalkylene diamine, barbituric acid and dialkylbarbituric acid. Dimethylaminobenzenesulphonamides corresponding to DE-A-3,135,113 are particularly preferred.

The coactivators are in general employed in an amount of 0.02 to 4% by weight, preferably 0.2 to 1% by weight, based on the amount of polymerisable compounds.

Other possible components for the compositions according to the invention are (meth)-acrylic acid esters which can form crosslinkings. (Meth)-acrylic acid esters which can form crosslinkings in general contain 2 or more polymerisable active double bonds in the molecule. Esters of (meth)-acrylic acid with di- to pentahydric alcohols having 2 to 30 carbon atoms may be mentioned as preferred. Epoxide (meth)acrylates and urethane (meth)acrylates are particularly preferred.

Examples which may be mentioned are the (meth)-acrylic acid esters of the formula

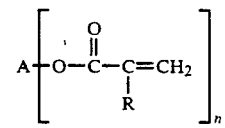

in which

A denotes a straight-chain, branched, cyclic, aliphatic, aromatic or mixed aliphatic-aromatic radical having 2 to 25 C atoms, which can be interrupted by —O— or NH bridges and can be substituted by hydroxyl, oxy, carboxyl, amino or halogen, R denotes H or methyl and n represents an integer from 2 to 8, preferably from 2 to 4.

Compounds of the following formulae may be mentioned as preferred:

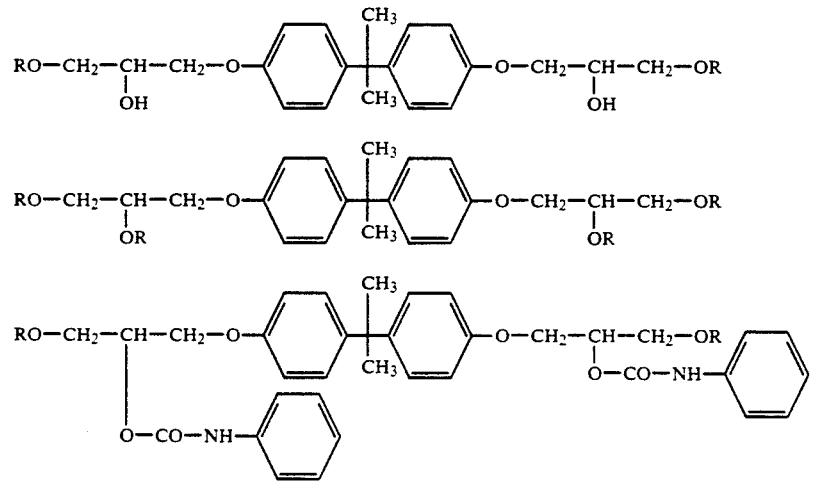

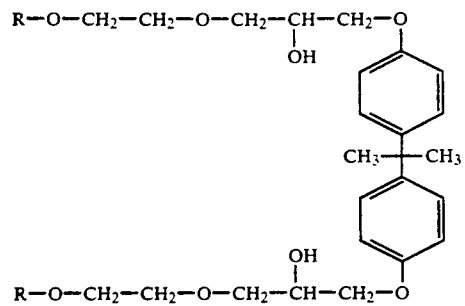
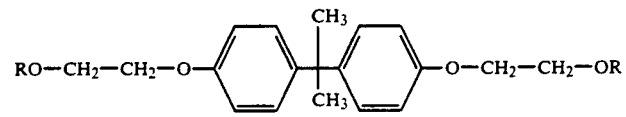
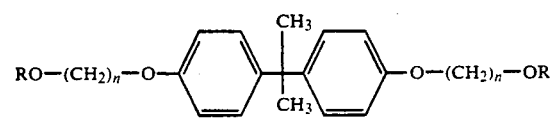
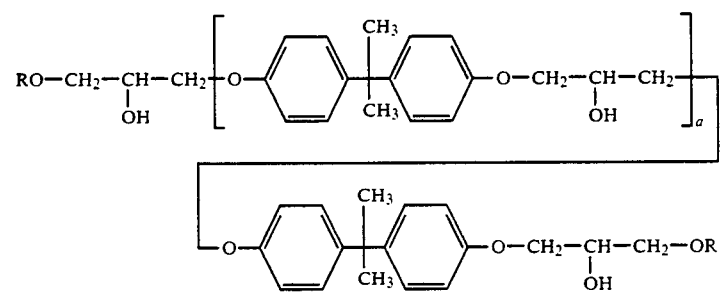
wherein a is a number from 1 to 4
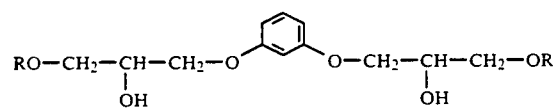
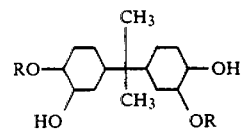
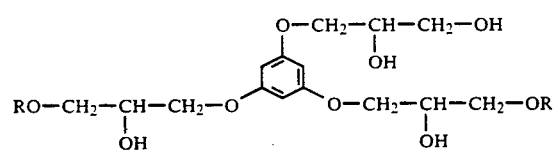
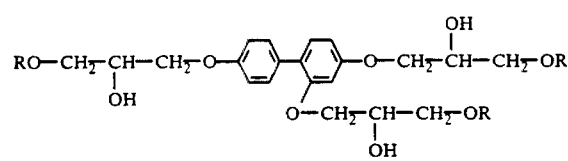
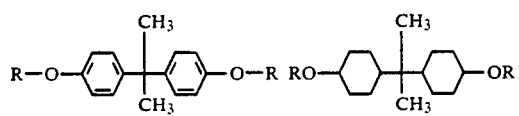
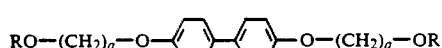
wherein a is a number from 1 to 4,
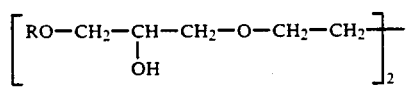
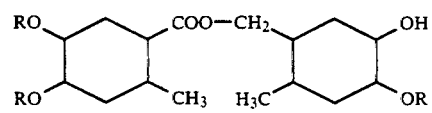
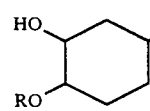
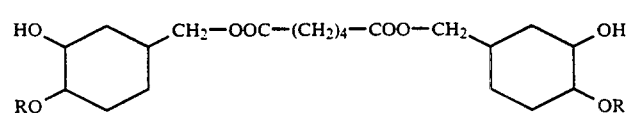

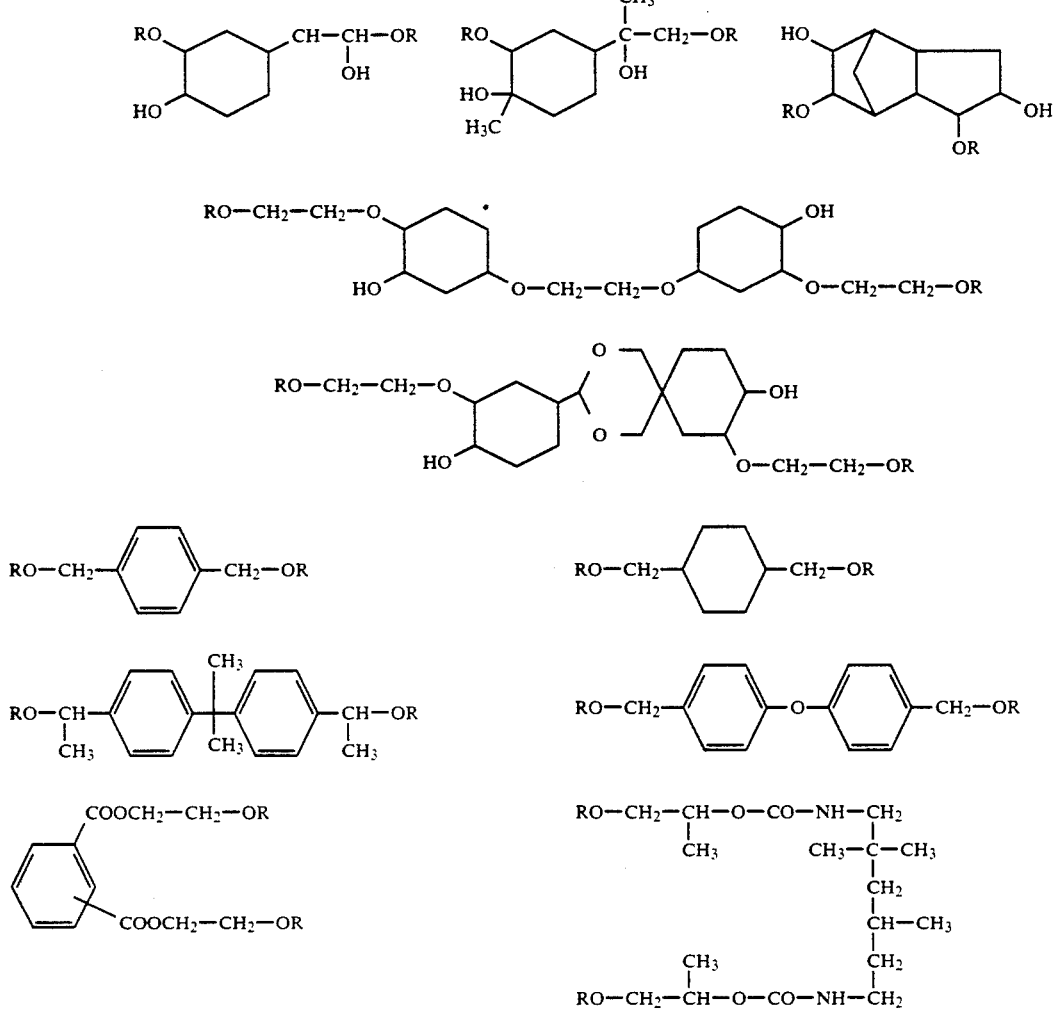
in the ortho-, meta- or para-form
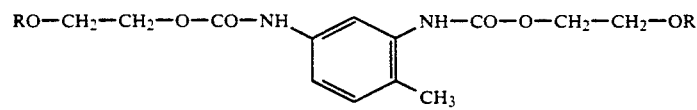
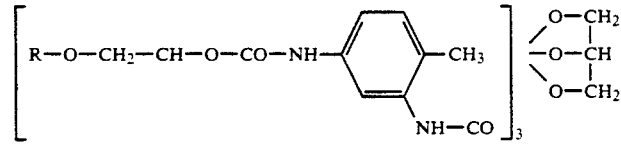
wherein R represents
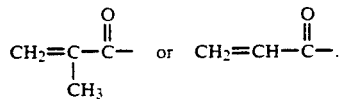
Derivatives of tricyclodecane (EP-A 0,023,686) and reaction products of polyols, diisocyanates and hydroxyalkyl methacrylates (DE-A 3,703,120, DE-A 3,703,080 and DE-A 3,703,130) may also be mentioned. The following monomers may be mentioned as examples:

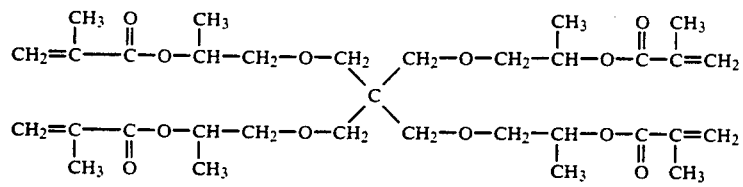
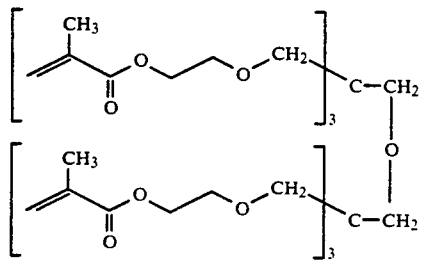
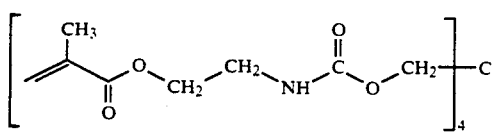
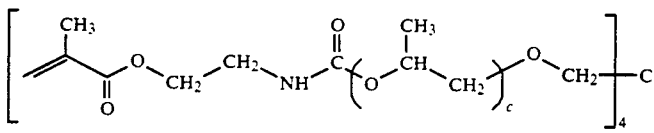
c = 1.225 (statistical mean value for 4 chains)
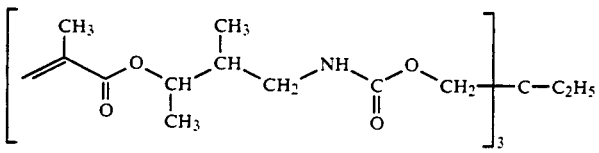
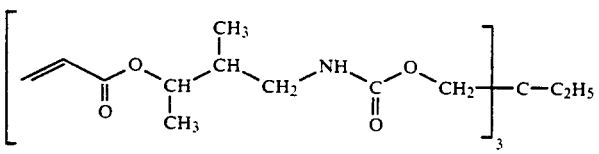
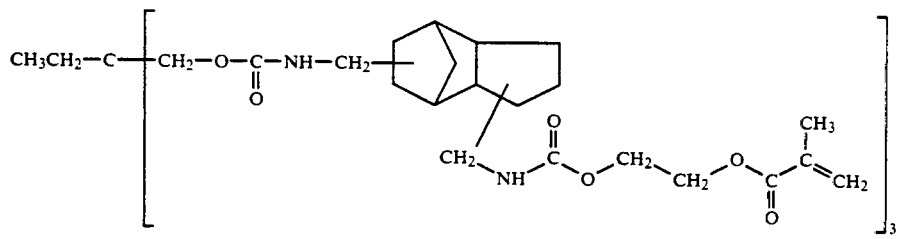
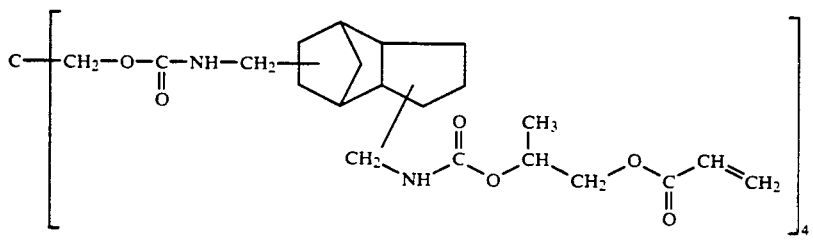

-continued
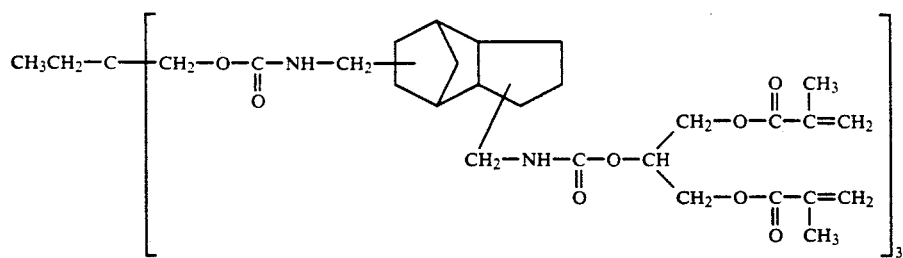
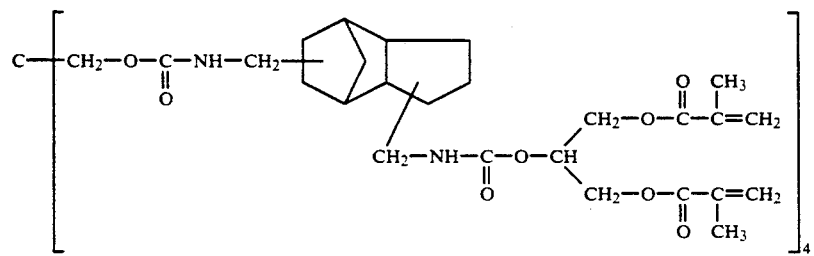
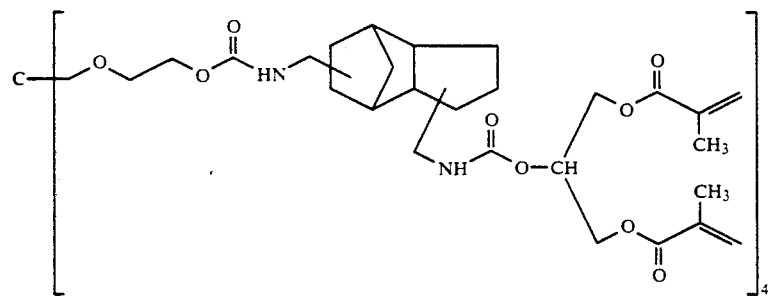
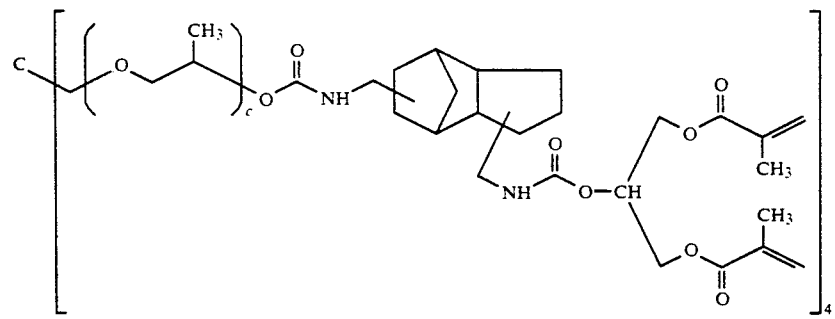
c = 1.225 (statistical mean value for 4 chains)
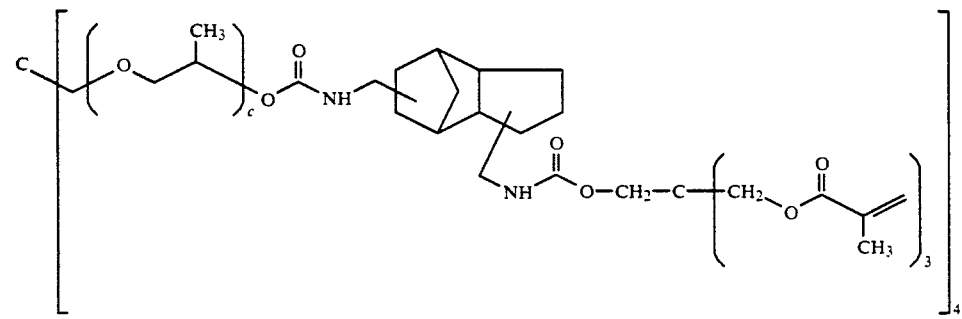
c = 1.225 (statistical mean value for 4 chains)

-continued
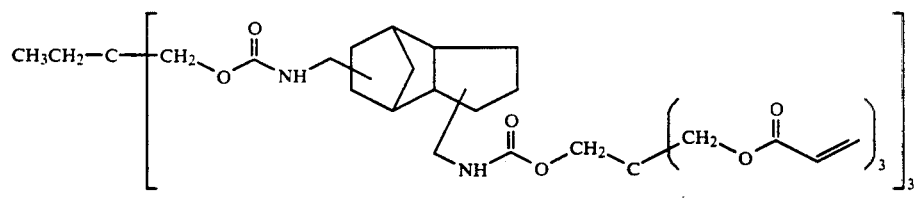
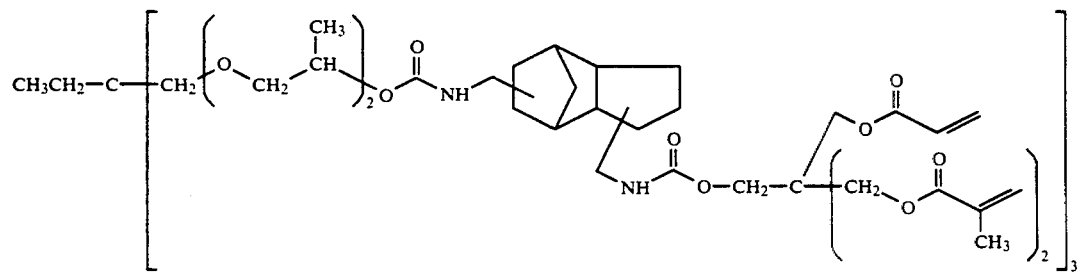
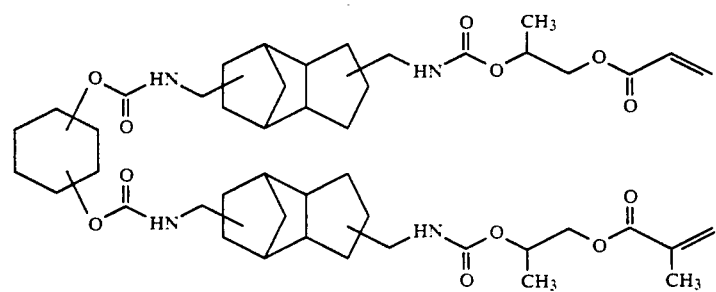
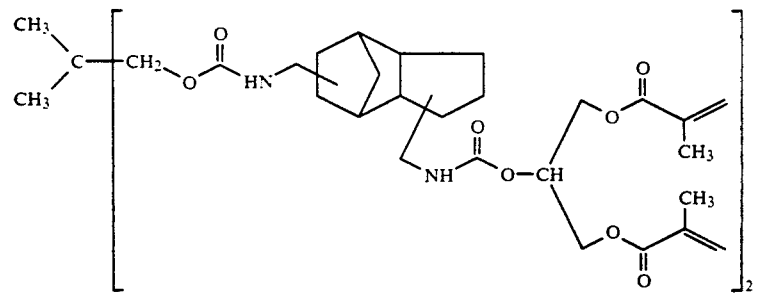
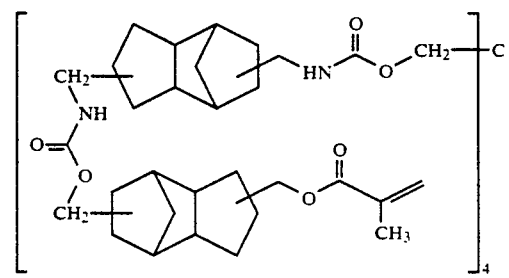

-continued
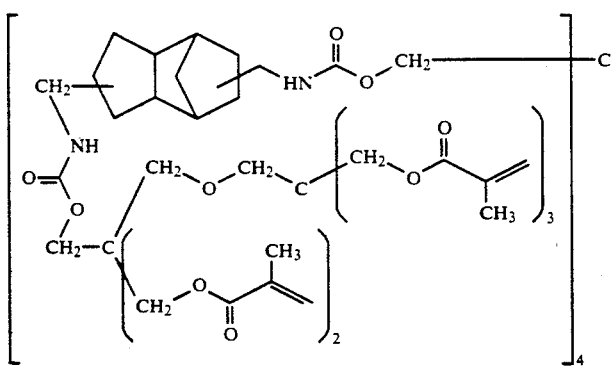
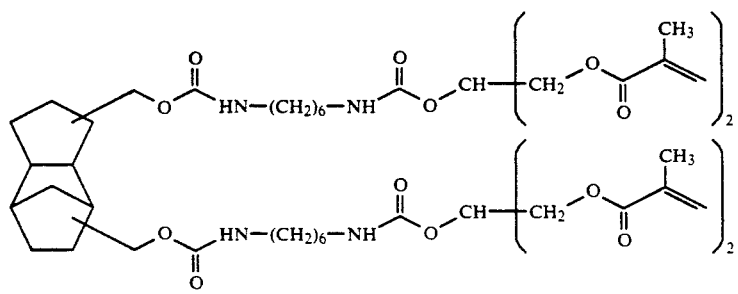
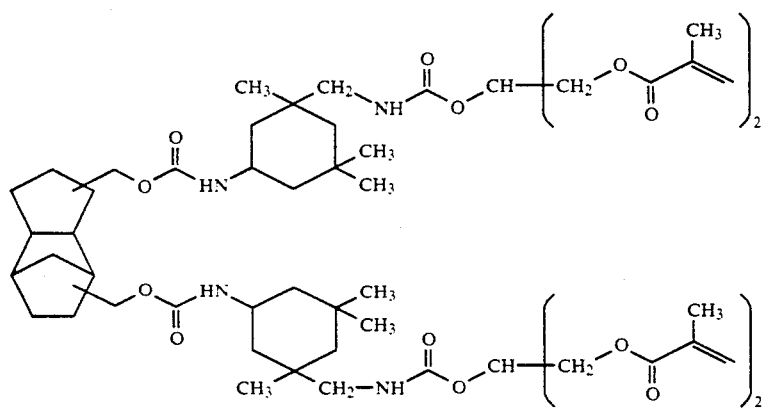
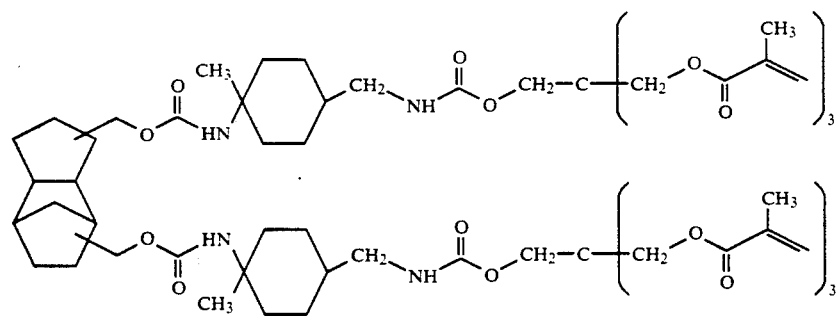
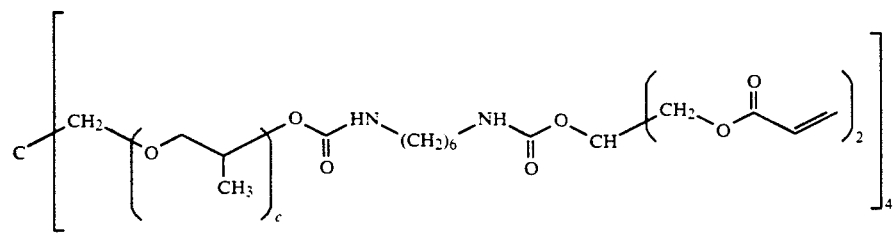
c = 1.225 (statistical mean value for 4 chains)

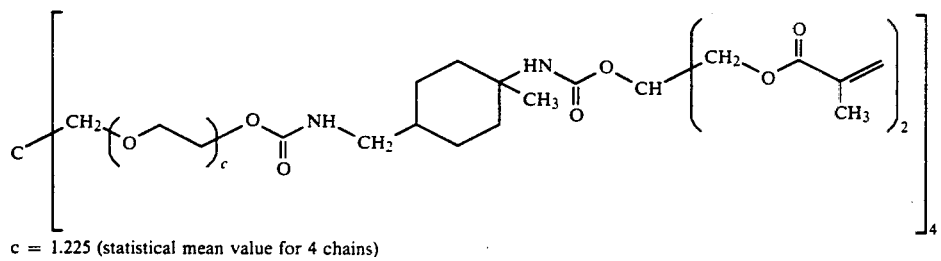

c = 1.225 (statistical mean value for 4 chains)

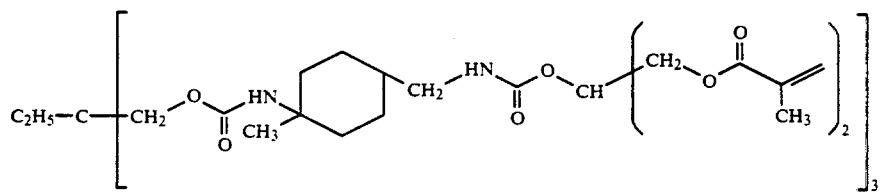

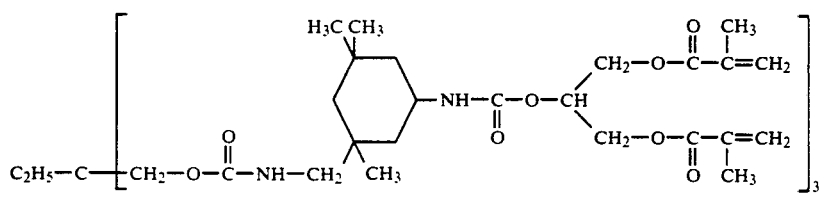

The so-called bis-GMA of the formula

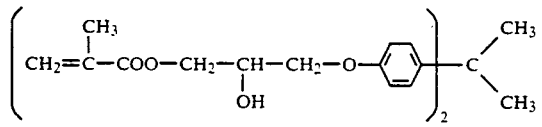 35 is particularly preferred as the methacrylic acid ester.

It is of course possible to employ mixtures of the various (meth)acrylic acid esters which can form cross-linkings. Examples which may be mentioned are mixtures of 20 to 70 parts by weight of bis-GMA and 30 to 80 parts by weight of triethylene glycol dimethacrylate.

The adhesive components according to this invention can furthermore comprise up to 10 parts by weight of customary additives, such as stabilisers, inhibitors and light stabilisers. The formulations according to the invention can be prepared by mixing the carboxamide (I), the solvent and the initiator and if appropriate the other components by vigorous stirring. The formulations according to the invention can be used as an adhesive component for the treatment of dental hard substance.

In a particular embodiment, the collagen-containing material is conditioned with a liquid having a pH in the range from 0.1 to 3.5 before the treatment with the formulation according to the invention. This liquid in general contains acids having a $pK_a$ value of less than 5, and if appropriate an amphoteric amino compound having a $pK_a$ value in the range from 9.0 to 10.6 and a $pK_b$ value in the range from 11.5 to 12.5. The conditioning liquid can comprise, for example, the following acids: phosphoric acid, nitric acid, pyruvic acid, citric acid, oxalic acid, ethylenediaminetetraacetic acid, acetic acid, tartaric acid and malic acid. Preferred amphoteric amino compounds which may be mentioned are compounds of the formula

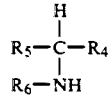

in which $R_4$ represents a carboxyl group, $R_5$ denotes hydrogen or a lower alkyl radical which is optionally substituted by hydroxyl, thio, methylthio, carboxyl, amino, phenyl, hydroxy-phenyl or the groups

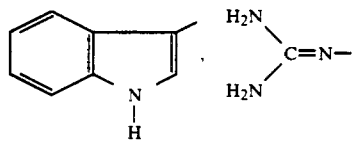

$R_6$ denotes hydrogen or phenyl and
wherein the radicals $R_4$ and $R_5$ can be bonded by a propyl radical, or in which $R_4$ represents hydrogen, $R_5$ represents the group

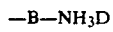

in which

B represents a divalent alkylene radical having 1 to 6 carbon atoms and

D represents halogen, and $R_6$ denotes hydrogen.

The following amphoteric amino compounds may be mentioned as examples: glycine, serine, threonine, cysteine, thyrosine, asparagine, glutamine, alanine, valine, leucine, isoleucine, proline, methionine, phenylalanine, tryptophan, lysine, arginine, histidine, N-phenylglycine, ethylenediamine hydrochloride, ethylenediamine hydrobromide, propylenediamine hydrochloride, propylenediamine hydrobromide, butylenediamine hydrochloride, butylenediamine hydrobromide, leucine hydrochloride and histidine hydrochloride. The conditioning liquid can furthermore comprise substances from the group comprising polyethylene glycols and metal hydroxides. In particular, the abovementioned polybasic acids can also be employed as partial metal salts, as long as free acid functions remain.

Conditioning liquids which comprise at least one of the acids from the group comprising pyruvic acid, ethylenediaminetetraacetic acid and citric acid and if appropriate an amphoteric amino compound from the group comprising glycine, N-phenylglycine and proline are particularly preferred.

The formulations according to the invention can be used, for example, as follows:

For a dental repair, for example, after mechanical cleaning of the collagen-containing dental material the conditioning liquid is first applied with a little cotton-wool and allowed to act for a short time (for example 60 seconds), and the dental material is rinsed with water and dried in a stream of air. The formulation according to the invention is then applied in a thin layer, for example with a small brush, and dried in a stream of air. After the treatment according to the invention, the actual filling composition, for example filling compositions of plastic which are customary in the dental sector (K. Eichner, "Zahnärztliche Werkstoffe und ihre Verarbeitung (Dental Materials and their Processing)", Volume 2, page 135 et seq., Hüthig Verlag, 5th edition 1985), is applied.

EXAMPLES 1 to 5

Preparation of carboxamides according to the invention

EXAMPLE 1

Trimellitic acid N-tert.-butyl-N-methacryloyloxyethylamide anhydride (VIII)

A solution of 185.27 g (1.000 mol) of N-tert.-butyl-2-aminoethyl methacrylate in 250 ml of dry methylene chloride was added dropwise to a solution of 210.57 g (1.000 mol) of benzenetricarboxylic acid anhydride chloride in 650 ml of dry methylene chloride and 202.38 g (2.000 mol) of dry triethylamine at −5° C., while stirring. After the mixture had been stirred at room temperature for three hours, the pale-coloured solid which had precipitated was filtered off with suction and the filtrate was extracted with water and dried.

The resulting methylene chloride solution contained the desired product (VIII) and could be employed directly for the hydrolysis.

After addition of 200 mg of 2,6-di-tert.-butylcresol, the resulting solution can be concentrated to give 280.31 g (78% of theory) of a yellowish solid comprising trimellitic acid N-tert.-butyl-N-methacryloyloxyethylamide anhydride (VIII).

Melting point: 58° C.

IR (KBr): $\nu=2960, 1860, 1783, 1720, 1640, 1380, 1240, 1195, 1150, 930, 889$ cm$^{-1}$. $^1$H-NMR (CDCl$_3$, 200 MHz): $\delta=1.59$ (s, 9 H, C(CH$_3$)$_3$), 1.87 (bs, 3 H, =CCH$_3$), 3.65 (t, J=6.3 Hz, 2H, NCH$_2$), 4.16 (t, J=6.3 Hz, 2 H, OCH$_2$), 5.64, 6.03 (2 bs, in each case 1 H, vinylidene H), 7.95 (m, 3 H, aromatic) ppm.

MS (70 eV): m/z=344 (M-CH$_3$), 273 (M-C$_3$H$_5$COOH), 217 (M-C$_3$H$_5$COOH-C$_4$H$_8$)

175 [structure: benzene ring with two fused —O—C(=O)— groups (anhydride) and a C≡O$^+$ group], 113 (C$_3$H$_5$—CO—O$^+$ [structure]), 69 (C$_3$H$_5$—C≡O$^+$), 57 (C$_4$H$_9^+$).

EXAMPLE 2

Trimellitic acid N-tert.-butyl-N-methacryloyloxyethylamide (IX)

200 ml of water were added to 700 ml of the methylene chloride solution from Example 1 containing 218.03 g (0.607 mol) of the anhydride (VIII) and the mixture was refluxed with vigorous stirring for 22 hours at 41° C. After drying and stabilising the organic phase with 100 mg of 2,6-di-tert.-butylcresol it was able to be concentrated to give 181.00 g (79% of theory) of a pale-coloured highly viscous oil of trimellitic acid N-tert.-butyl-N-methacryloyloxyethylamide (IX). The oil obtained solidified on cooling and was able to be further purified by being extracted from a methylene chloride solution using aqueous sodium carbonate solution, acidifying the aqueous phase with dilute hydrochloric acid and re-extracting the product (IX) in a methylene chloride phase. Melting point: 74° C.

IR (KBr): $\nu=3500-2500, 2950, 1720, 1630, 1600, 1400, 1365, 1290, 1192, 1158$ cm$^{-1}$.

$^1$H-NMR (CDCl$_3$, 200 MHz): $\delta=1.58$ (s, 9 H, C(CH$_3$)$_3$), 1.90 (bs, 3 H, =CCH$_3$), 3.65 (t, J=6.0 Hz, 2 H, NCH$_2$), 4.13 (t, J=6.0 Hz, 2 H, OCH$_2$), 5.61, 6.05 (2 m, in each case 1 H, vinylidene H), 7.52 (m, 3 H, aromatic H, COOH), 7.82 (m, 1 H, aromatic H) ppm.

MS (70 eV-silylated): m/z=506 (M-CH$_3$), 435 (M-C$_3$H$_5$COOH), 379 (M-C$_3$H$_5$COOH—C$_4$H$_8$), 337 [structure: benzene ring with two TMS—O$_2$C groups and a C≡O$^+$ group], 147 (Me$_3$Si—O—SiMe$_2$), 113 (C$_3$H$_5$—CO—O$^+$ [structure]).

73 (TMS$^+$), 69 (C$_3$H$_5$—C≡O$^+$), 57 (C$_4$H$_9^+$).

EXAMPLE 3

Pyromellitic acid 1,4-di-(N-tert.-butyl-N-methacryloyloxyethylamide) (X) Pyromellitic acid 1,3-di(N-tert.-butyl-N-methacryloyloxyethylamide) (XI)

A solution of 370.54 g (2.000 mol) of N-tert.-butyl-2-aminoethyl methacrylate in 370 ml of dry methylene chloride was added dropwise to a suspension of 218.12 g (1.000 mol) of pyromellitic acid dianhydride, 750 ml of dry methylene chloride and 505.95 g (5.000 mol) of dry triethylamine, with vigorous stirring. A brown solution was formed during this procedure, while heating gently, and was stirred at 41° C. for one hour, poured into 1 l of water and acidified with half-concentrated sulphuric acid.

After the solid which had precipitated had been separated off, the methylene chloride phase was extracted with water, dried and concentrated to give 314.70 g (53% of theory) of a beige-coloured solid of a mixture of the para- and meta-isomers (X) and (XI) of pyromellitic acid di(N-tert.-butyl-N-methacryloyloxyethylamide). A purified white solid was obtained by taking up the resulting product in aqueous sodium carbonate solution, extracting the mixture with methylene chloride and precipitating the product again with half-concentrated sulphuric acid.

Melting point: 121° C.

IR(KBr): $\nu = 3400$-2500, 1715, 1618, 1411, 1405, 1360, 1330, 1300, 1213, 1172, 1131, 955, 780 cm$^{-1}$.

$^1$H-NMR (CDCl$_3$, 200 MHz): $\delta = 1.57$ (s, 18 H, C(CH$_3$)$_3$), 1.86 (bs, 6 H, =CCH$_3$), 3.45 (m, 4 H, NCH$_2$), 4.12 (m, 4 H, OCH$_2$), 5.53, 5.98 (2 m, in each case 2 H, vinylidene H), 7.89 (bs, 2 H, COOH), 8.41 (s, 2H, aromatic H) ppm.

FAB-MS (glycerol-DMF): m/z=
589 ([M+H]$^+$)
587 ([M−H]$^-$).

EXAMPLE 4

Pyromellitic acid (N-tert.-butyl-N-methacryloyloxyethylamide) (XII)

A solution of 185.27 g (1.000 mol) of N-tert.-butyl-2-aminoethyl methacrylate in 250 ml of xylene was added to a mixture of 218.12 g (1.000 mol) of pyromellitic acid dianhydride, 171.50 g (1.200 mol) of triethylamine and 2200 ml of xylene at room temperature, while stirring, and the mixture was heated at 50° C. for one hour. The mixture was filtered, the filtrate was poured into ice-water and, for hydrolysis, the mixture was acidified with half-concentrated sulphuric acid and stirred for 30 minutes. The precipitate which had separated out was filtered off with suction and recrystallised from ethyl acetate to give 232.05 g (about 55% of theory) of a white solid which, in addition to the pyromellitic acid (N-tert.-butyl-N-methacryloyloxyethylamide) (XII), contained a relatively small amount of the double reaction products (X) and (XI) of Example 3.

Melting point: 215° C.

IR (KBr): $\nu = 3500$-2500, 1710, 1605, 1400, 1345, 1316, 1282, 1194, 1153, 932, 752 cm$^{-1}$.

$^1$H-NMR (d$_6$-DMSO, 200 MHz): $\delta = 1.49$ (s, 9H, C(CH$_3$)$_3$), 1.78 (bs=C-CH$_3$), 3.44 (m, 2 H, NCH$_2$), 4.06 (m, 2 H, OCH$_2$), 5.61, 5.89 (2 m, in each case 1 H, vinylidene H), 7.62, 8.29 (2 s, in each case 1 H, aromatic H), 8.40 (bs, 3 H, COOH) ppm.

FAB-MS (glycerol-DMF): m/z=
422 ([M+H]$^+$),
420 ([M−H]$^-$).

EXAMPLE 5

Benzene-1,3-dicarboxylic acid-4(carboxylic acid N-tert.-butyl-N-methacryloyloxyethylamide) (XIII) Benzene-1,4-dicarboxylic acid-5(carboxylic acid N-tert.-butyl-N-methacryloyloxyethylamide) (XIV)

A solution of 185.27 g (1.000 mol) of N-tert.-butyl-2-aminoethyl methacrylate in 250 ml of methylene chloride was added dropwise to a mixture of 192.13 g (1.000 mol) of benzenetricarboxylic acid anhydride, 500 ml of dry methylene chloride and 303.57 g (3.000 mol) of dry triethylamine at room temperature, while stirring. After the mixture had been stirred at 41° C. for 4 hours, it was poured into 3 l of water, the mixture was acidified with half-concentrated sulphuric acid and the organic phase was separated off. The aqueous phase was extracted with methylene chloride and, after drying and stabilisation with 350 mg of 2,6-di-tert.-butylcresol, the combined organic phases were concentrated to give 284.60 g (78% of theory) of a beige-coloured solid of a mixture of the two isomers (XIII) and (XIV) of benzenetricarboxylic acid mono-(N-tert.-butyl-N-methacryloyloxyethylamide).

Melting point: 71° C.

IR (KBr): $\nu = 3400$-2400, 1700, 1610, 1370, 1283, 1161, 1040, 1010, 932, 752 cm$^{-1}$.

$^1$H-NMR(CDCl$_3$, 200 MHz): for XIII: 1.58 (bs, 9 H, C(CH$_3$)$_3$), 1.82 (bs, 3 H, =CCH$_3$), 3.32 (m, 2 H, NCH$_2$), 4.51 (m, 2 H, OCH$_2$), 5.49, 5.95 (2 m, in each case 1 H, vinylidene H), 7.1 (m, 2 H, COOH), 8.15, 8.75 (m, 3 H, aromatic H) ppm.

for XIV: $\delta = 1.43$ (s, 9 H,C(CH$_3$)$_3$), 1.8 (bs, 3 H, =CCH$_3$), 3.48 (m, 2 H, NCH$_2$), 4.1 (m, 2 H, OCH$_2$), 5.44, 6.03 (2 m, in each case 1 H, vinylidene H), 7.1 (m, 2 H, COOH), 8.0-8.6 (m, 3 H, aromatic H) ppm.

EXAMPLES 6 to 10

Preparation of the formulations for use as an adhesive

The adhesives according to the invention are produced by intensive mixing of the constituents listed in the following examples.

EXAMPLE 6

37.5 g of water
50.0 g of tetrahydrofuran
12.5 g of trimellitic acid N-tert.-butyl-N-methacryloyloxyethylamide (IX) according to Example 2
0.02 g of camphorquinone

EXAMPLE 7

27.3 g of water
63.6 g of tetrahydrofuran
9.1 g of trimellitic acid N-tert.-butyl-N-methacryloyloxyethylamide anhydride (VIII) according to Example 1
0.02 g of camphorquinone

EXAMPLE 8

40.0 g of water
48.0 g of tetrahydrofuran
8.4 g of trimellitic acid N-tert.-butyl-N-methacryloyloxyethylamide (IX) according to Example 2
3.6 g of trimellitic acid N-tert.-butyl-N-methacryloyloxyethylamide anhydride (VIII) according to Example 1
0.02 g of camphorquinone

EXAMPLE 9

93.7 g of ethanol
6.3 g of pyromellitic acid di(N-tert.-butyl-N-methacryloyloxyethylamide (p- and m-isomers (X) and (XI) according to Example 3)
0.01 g of camphorquinone

EXAMPLE 10

43.5 g of water
43.5 g of tetrahydrofuran oyloxyethylamide) (XII) according to Example 4

3.5 g of pyromellitic acid di(N-tert.-butyl-N-methacryloyloxyethylamide (p- and m-isomers (X) and (XI) according to Example 3)

0.02 g of camphorquinone

EXAMPLE 11

Use test, bonding strength

The activity and suitability of the adhesives (Examples 6-10) is checked by determination of the shear bonding strength to dentine. Human teeth which have been kept in 1% strength chloramine solution for a maximum of three months after the extraction are used. Before being used in the test, the teeth are kept in physiological saline solution for at least three and not more than ten days, after thorough washing under running water. On the day before their use in the bonding test, the teeth are embedded individually, lying on an approximal side, with epoxy resin (®LEKUTHERM X 20, hardener T 3) in cylindrical rubber moulds of 25 mm diameter and 12 mm height. The teeth are ground by wet grinding on SiC papers of grains 240, 320, 400 and finally 600 to the extent that an adequately large dentine surface close to the enamel is exposed for binding to a cylinder of plastic of 3.5 mm diameter. After rinsing with deionised water and drying in a stream of air, the conditioning solution ®GLUMA 1 Cleanser is applied with a cotton-wool pellet using a rubbing movement for 30 seconds and the teeth are rinsed with water and dried, before the adhesive is applied with a brush, left on the surface for 30 seconds and then dried thoroughly in a stream of compressed air. One drop of ®GLUMA 4 Sealer is then applied and blown into a thin layer with compressed air. The sample pretreated in this way is firmly clamped in a clamping device under a divisible Teflon mould having a cylindrical receptacle 3.5 mm wide and 1 mm in height. The cylindrical mould is then filled with the plastic filling material ®PEKAFILL (U) using a syringe, and the filling material is covered with a strip which is impermeable to $O_2$ and activated for 60 seconds under the supported light discharge opening of a ®TRANSLUX CL (Kulzer) polymerisation lamp. The sample is then immediately removed from the holder. The Teflon mould is removed and the sample is kept in warm water at 23° C. for 15 minutes, until shearing stress is initiated, this being effected with the aid of a pressure piston parallel to and close to the surface of the embedded tooth at an advanced speed of 1 mm/minute until separation occurs. The shear bonding strength to the dentine is the quotient of the pressure and contact area on the tooth, and is in each case determined on 5 samples and stated as the mean value and standard deviation thereof.

The dentine side of the separated sample is inspected under a reflected light microscope to evaluate the cause of fracture.

EXAMPLE 12

Use test, tooth cavity

To simulate the clinical use of adhesives and filling materials of plastics, cavities are prepared and filled in extracted teeth with a previous history as in Example 11. The adaptation of the filling material at the edge of the cavity is determined as a measure of the effectiveness.

The extracted teeth are subjected to wet grinding on an undamaged aproximal side on SiC paper of grains 240, 320, 400 and 600 until a sufficiently large area of dentine is exposed for accommodation of a cylindrical cavity about 3 mm wide. The cavity is prepared down to a depth of about 1.5 mm using customary dentistry preparation diamonds of medium grain size with copious cooling with water, and is then rinsed out with water and dried. The cavity is cleaned with an impregnated cotton-wool pellet for 30 seconds as in the preceding example and is then washed out and dried, before the adhesive is brushed on, left for 30 seconds and finally dried. The ®GLUMA 4 Sealer is then applied The excess is carefully removed with compressed air before the cavity is filled with the plastic filling material ®PEKAFILL (U) using a syringe. The excess is covered with a strip which is impermeable to $O_2$ before activation (60 seconds) using the ®TRANSLUX CL (Kulzer) photopolymerisation apparatus. Immediately after the polymerisation, the filled tooth is kept in warm water at 23° C. for 15 minutes. Thereafter, the excess is removed by grinding on moist SiC paper of grains 400 and 600. During this operation, about 0.1 mm of the height of the cavity is worn away. The tooth is rinsed with water, dried in a stream of air and immediately inspected under a reflected light microscope at 500-fold magnification. The maximum width of any gap present at the edge is measured with the aid of a screw eyepiece micrometer. The average maximum gap width of in each case 5 fillings is stated as the measurement value. Microscopic examination of individual teeth was in all cases concluded in less than 10 minutes. It was thus ensured that the gaps measured at the edges had not formed or were not influenced in width by dehydration of the dentine.

Results of the technological investigations

The good effectiveness of the formulation according to Examples 6 to 10 could be demonstrated by means of the use test described in Examples 11 and 12.

When the cause of fracture was evaluated under a light microscope, cohesive fractures in the dentine or in the plastic were often observed, that is to say the gluе-ings produced using the adhesive components according to the invention were stronger than the glued parts of the join themselves. This shows the good performance of the adhesive components according to the invention.

Fillings which were exclusively free from gaps at the edges were even obtained by the method described using the formulation according to Example 6. The shear bonding strength was determined formally as 12.1±3.5 N/mm², the fracture taking place in the dentine or plastic, as mentioned above, that is to say no adhesive failure being achievable.

We claim:

1. N-Alkyl-N-(meth)acryloyloxyalkylcarboxamides of the formula (I)

in which

X represents an N-alkyl-N-(meth)acryloyloxyalkyl-carboxamide of the formula

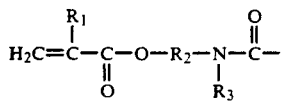

wherein
$R_1$ denotes hydrogen or methyl,
$R_2$ denotes a divalent aliphatic radical ($C_2$–$C_6$) and
$R_3$ denotes a monovalent aliphatic radical ($C_1$–$C_4$),
Y represents COOH, it also being possible for adjacent groups Y to be linked to form an anhydride group (—CO—O—CO—)
Z represents H, X or, if Y denotes COOH, Y and
Ph represents a tri- or tetrasubstituted benzene ring (1,2,3-/1,2,4- or 1,2,4,5-substitution) or a tri- or tetrasubstituted naphthalene ring (1,2,6-/1,4,5-/2,3,6-/1,4,5,8- or 2,3,6,7-substitution).

2. N-Alkyl-N-(meth)acryloyloxyalkylcarboxamides of the formula (II)

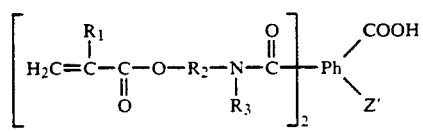

in which
$R_1$ denotes hydrogen or methyl,
$R_2$ denotes a divalent aliphatic radical ($C_2$–$C_6$) and
$R_3$ denotes a monovalent aliphatic radical ($C_1$–$C_4$),
Z' denotes hydrogen or COOH and
Ph represents a tri- or tetrasubstituted benzene ring (1,2,3-/1,2,4- or 1,2,4,5-substitution) or a tri- or tetrasubstituted naphthalene ring (1,2,6-/1,4,5-/2,3,6-/1,4,5,8- or 2,3,6,7-substitution).

3. N-Alkyl-N-(meth)acryloyloxyalkylcarboxamides of the formula (III)

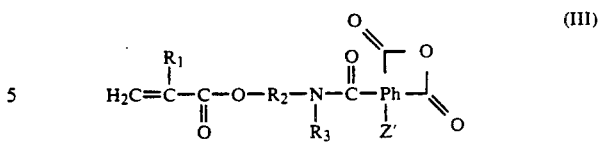

in which
$R_1$ denotes hydrogen or methyl,
$R_2$ denotes a divalent aliphatic radical ($C_2$–$C_6$) and
$R_3$ denotes a monovalent aliphatic radical ($C_1$–$C_4$),
Z' denotes hydrogen or COOH and
Ph represents a benzene ring which is tri- or tetrasubstituted (1,2,3-/1,2,4- or 1,2,4,5-substitution) or a tri- or tetrasubstituted naphthalene ring (1,2,6-/1,4,5-/2,3,6-/1,4,5,8- or 2,3,6,7-substitution).

4. N-Alkyl-N-(meth)acryloyloxyalkylcarboxamides of the formula (IV)

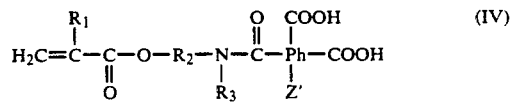

in which
$R_1$ denotes hydrogen or methyl,
$R_2$ denotes a divalent aliphatic radical ($C_2$–$C_6$) and
$R_3$ denotes a monovalent aliphatic radical ($C_1$–$C_4$),
Z' denotes hydrogen or COOH and
Ph represents a tri- or tetrasubstituted benzene ring (1,2,3-/1,2,4- or 1,2,4,5-substitution) or a tri- or tetrasubstituted naphthalene ring (1,2,6-/1,4,5-/2,3,6-/1,4,5,8- or 2,3,6,7-substitution).

5. Compositions containing carboxamides according to claim 1, a solvent and if appropriate an initiator.

6. Compositions containing carboxamides according to claim 1, a solvent and if appropriate an initiator, said initiator being selected from mono- or dicarbonyl compounds which form free radicals.

7. Compositions containing carboxamides according to claim 1, a solvent and if appropriate an initiator, comprising a coactivator.

8. Compositions containing carboxamides according to claim 1, a solvent and if appropriate an initiator, additionally comprising (meth)acrylic acid esters which can form crosslinkings.

* * * * *